(12) United States Patent
Inukai et al.

(10) Patent No.: US 6,428,481 B1
(45) Date of Patent: Aug. 6, 2002

(54) BLOOD PRESSURE MONITOR APPARATUS

(75) Inventors: Hidekatsu Inukai, Nagoya; Keizoh Kawaguchi, Komaki; Tomohiro Nunome, Komaki; Akihiro Yokozeki, Komaki, all of (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/580,639

(22) Filed: May 30, 2000

(51) Int. Cl.$^7$ .................................................. A61B 5/00
(52) U.S. Cl. ........................................ 600/485; 600/500
(58) Field of Search .......................... 600/481, 483–485, 600/490, 492–495, 500–502, 526

(56) References Cited

U.S. PATENT DOCUMENTS

| | | | |
|---|---|---|---|
| 4,967,756 A | * 11/1990 | Hewitt | 600/493 |
| 5,131,400 A | 7/1992 | Harada et al. | |
| 6,193,654 B1 | * 2/2001 | Richardson et al. | 600/301 |
| 6,196,974 B1 | * 3/2001 | Miwa | 600/494 |

FOREIGN PATENT DOCUMENTS

| | | |
|---|---|---|
| EP | 0 829 227 A2 | 3/1998 |
| EP | 0 956 815 A1 | 11/1999 |
| EP | 0 956 816 A1 | 11/1999 |
| EP | 0 956 817 A1 | 11/1999 |
| EP | 0 993 803 A1 | 4/2000 |

* cited by examiner

*Primary Examiner*—Robert L. Nasser
(74) *Attorney, Agent, or Firm*—Oliff & Berridge, PLC

(57) ABSTRACT

A device for monitoring the blood pressure of a living subject, including a pulse-wave-propagation-velocity-relating information obtaining device for successively obtaining pulse-wave-propagation-velocity-relating information which relates to a pulse-wave propagation velocity at which a pulse wave propagates in an artery of the subject, a pulse-period-relating information obtaining device for successively obtaining pulse-period-relating information which relates to a pulse period of the subject, a peripheral-blood-volume-relating information obtaining device for successively obtaining peripheral-blood-volume-relating information which relates to a volume of blood which flows in a peripheral body portion of the subject, and an abnormality judging device for judging that the blood pressure of the subject is abnormal when at least one of the pulse-wave-propagation-velocity-relating information, pulse-period-relating information, and peripheral-blood-volume-relating information does not fall within a corresponding one of a first, a second and a third reference range.

4 Claims, 6 Drawing Sheets

BLOOD PRESSURE MONITOR APPARATUS

The present application is based on Japanese Patent Application No. 10-337697 filed Nov. 27, 1998, the contents of which are incorporated hereinto by reference.

BACKGROUND OF THE INVENTION

1. Field of the Invention

The present invention relates to a blood pressure monitor apparatus which monitors a blood pressure of a living subject based on pulse-wave-propagation-velocity-relating information which relates to a propagation velocity of a pulse wave which propagates through an artery of a subject, pulse-period-relating information which relates to a period of a pulse of a subject, and peripheral-blood-volume-relating information which relates to a volume of blood which flows in a peripheral body portion of a subject.

2. Discussion of the Related Art

As pulse-wave-propagation-velocity-relating information, there is known a propagation time DT during which a pulse wave propagates between predetermined two portions of an artery, or a propagation velocity $V_M$ (m/s) at which a pulse wave propagates through an artery. It is generally known that such pulse-wave-propagation-velocity-relating information is substantially proportional to a blood pressure BP (mmHg) of a living subject within a predetermined range. In view of this, there is proposed a blood pressure monitor apparatus which monitors a change or fluctuation of the blood pressure of the subject by monitoring whether or not successively obtained pulse-wave-propagation-velocity-relating information is greater than a predetermined upper reference value or smaller than a predetermined lower reference value, and judges that the blood pressure has changed and starts a blood pressure measurement using a cuff when the obtained pulse-wave-propagation-velocity-relating information is greater than the predetermined upper reference value or smaller than the predetermined lower reference value.

However, the pulse-wave-propagation-velocity-relating information is not proportional to the blood pressure in an entire blood pressure range. Namely, the correlation between the pulse-wave-propagation-velocity-relating information and the blood pressure is considerably low in a considerably low blood pressure range and a considerably high blood pressure range. Accordingly, the conventional blood pressure monitor apparatus which monitors the change of the blood pressure based on the pulse-wave-propagation-velocity-relating information is not capable of accurately detecting the change of the blood pressure in the entire blood pressure range.

SUMMARY OF THE INVENTION

It is therefore an object of the present invention to provide a blood pressure monitor apparatus which is capable of accurately detecting a change or fluctuation of the blood pressure of a living subject in the entire blood pressure range.

As a result of an extensive study by the inventors of the present invention, it has been found that the change of the blood pressure can be detected with high accuracy in the entire blood pressure range if other information which is correlative with the blood pressure is used to monitor the blood pressure, in addition to the pulse-wave-propagation-velocity-relating information. Such information includes pulse-period-relating information which relates to a period of a pulse of the subject, such as a pulse period and a heart rate, and peripheral-blood-volume-relating information which relates to a volume of blood flowing in a peripheral body portion of the subject, such as an amplitude and an area of a pulse wave detected from the peripheral body portion of the subject.

The above-indicated object of the present invention may be attained according to a principle of the invention, which provides a blood pressure monitor apparatus for monitoring a blood pressure of a living subject, comprising: pulse-wave-propagation-velocity-relating information obtaining means for successively obtaining pulse-wave-propagation-velocity-relating information which relates to a pulse-wave propagation velocity at which a pulse wave propagates in an artery of the subject; pulse-period-relating information obtaining means for successively obtaining pulse-period-relating information which relates to a pulse period of the subject; peripheral-blood-volume-relating information obtaining means for successively obtaining peripheral-blood-volume-relating information which relates to a volume of blood which flows in a peripheral body portion of the subject; and abnormality judging means for judging that the blood pressure of the subject is abnormal when at least one of the pulse-wave-propagation-velocity-relating information, pulse-period-relating information, and peripheral-blood-volume-relating information does not fall within a corresponding one of a first, a second and a third reference range.

In the blood pressure monitor apparatus constructed as described above, the change of the blood pressure of the subject can be detected with high accuracy in the entire blood pressure range since the blood pressure of the subject is judged to be abnormal when at least one of the pulse-period-relating information and the peripheral-blood-volume-relating information does not fall within a corresponding one of the second and third reference ranges, even if the pulse-wave-propagation-velocity-relating information may fall within the corresponding first reference range.

In a preferred form of the present invention, the first, second, and third reference ranges have a first, a second, and a third upper limit value, respectively. The first, second, and third reference ranges may or may not have a lower limit value.

In a preferred form of the present invention, the first, second, and third reference ranges have a first, a second, and a third lower limit value, respectively. The first, second, and third reference ranges may or may not have an upper limit value.

In a preferred form of the present invention, the first, second, and third reference ranges have a first, a second, and a third upper limit value, respectively, and a first, a second, and a third lower limit value, respectively.

In a preferred form of the present invention, the first, second, and third upper limit values are a common value. The first, second, and third upper limit values may be different from one another.

In a preferred form of the present invention, the first, second, and third lower limit values are a common value. The first, second, and third lower limit values may be different from one another.

In a preferred form of the present invention, the blood pressure monitor apparatus further comprises blood pressure measuring means which includes a cuff and which measures a blood pressure of the subject by changing a pressing pressure of the cuff applied to a body portion of the subject, and the abnormality judging means starts a blood pressure measurement of the blood pressure measuring means when the blood pressure of the subject is judged to be abnormal.

The blood pressure monitor apparatus constructed according to the above arrangement starts the blood pressure measurement of the blood pressure measuring means when at least one of the pulse-period-relating information and the peripheral-blood-volume-relating information does not fall within a corresponding one of the second and third reference ranges, even if the pulse-wave-propagation-velocity-relating information may fall within the corresponding first reference range. Accordingly, the present blood pressure monitor apparatus is capable of quickly obtaining the blood pressure of the subject with high reliability in the entire blood pressure range when the blood pressure of the subject has changed.

In a preferred form of the present invention, the pulse-wave-propagation-velocity-relating information obtaining means comprises first estimated blood pressure determining means for successively determining, as the pulse-wave-propagation-velocity-relating information, a first estimated blood pressure value $EBP_1$, based on a pulse-wave propagation time, by utilizing a predetermined relationship between first estimated blood pressure value $EBP_1$ and pulse-wave propagation time $DT_{RP}$, the relationship being represented by an equation: $EBP_1=\alpha_1(1/DT_{RP})+\alpha_1$, wherein $\alpha_1$ and $\beta_1$ represent coefficients, the pulse-period-relating information obtaining means comprises second estimated blood pressure determining means for successively determining, as the pulse-period-relating information, a second estimated blood pressure value $EBP_2$, based on a pulse period of the subject, by utilizing a predetermined relationship between second estimated blood pressure value $EBP_2$ and pulse period RR, the relationship being represented by an equation: $EBP_2=\alpha_2RR+\beta_2$, wherein $\alpha_2$ and $\beta_2$ represent coefficients, and the peripheral-blood-volume-relating information obtaining means comprises third estimated blood pressure determining means for successively determining, as the peripheral-blood-volume-relating information, a third estimated blood pressure value $EBP_3$, based on a pulse-wave area, by utilizing a predetermined relationship between third estimated blood pressure value $EBP_3$ and pulse-wave area VR, the relationship being represented by an equation: $EBP_3=\alpha_3VR+\beta_3$, wherein $\alpha_3$ and $\beta_3$ represent coefficients.

In a preferred form of the present invention, pulse-wave-propagation-velocity-relating information obtaining means comprises an electrocardiographic-waveform detecting device which includes a plurality of electrodes adapted to be attached to a body portion of the subject and detects an electrocardiographic waveform indicative of an action potential of a cardiac muscle of the subject through the electrodes, and a photoelectric-pulse-wave detecting device which includes a plurality of light-emitting elements and a light-receiving element, each of the light-emitting elements emitting, toward a body surface of the subject, a light having a wavelength which is reflected by hemoglobin present in the blood of the subject, the light-receiving element receiving the light scattered by the hemoglobin from the body surface of the subject, the photoelectric-pulse-wave detecting device detecting a photoelectric pulse wave indicative of the volume of the blood flowing in the body surface, the pulse-wave propagation time ($DT_{RP}$) representing a time difference between a predetermined point of a pulse of the electrocardiographic waveform detected by the electrocardiographic-waveform detecting device, and a predetermined point of a waveform of a corresponding pulse of the photoelectric pulse wave detected by the photoelectric-pulse-wave detecting device.

In a preferred form of the present invention, the pulse-period-relating information obtaining means comprises an electrocardiographic-waveform detecting device which includes a plurality of electrodes adapted to be attached to a body portion of the subject and detects an electrocardiographic waveform indicative of an action potential of a cardiac muscle of the subject through the electrodes, the pulse period (RR) representing an interval between successive two R-waves of the electrocardiographic waveform detected by the electrocardiographic-waveform detecting device.

In a preferred form of the present invention, the peripheral-blood-volume-relating information obtaining means comprises a photoelectric-pulse-wave detecting device which includes a plurality of light-emitting elements and a light-receiving element, each of the light-emitting elements emitting, toward a body surface of the subject, a light having a wavelength which is reflected by hemoglobin present in the blood of the subject, the light-receiving element receiving the light scattered by the hemoglobin from the body surface of the subject, the photoelectric-pulse-wave detecting device detecting a photoelectric pulse wave indicative of the volume of the blood flowing in the body surface, the pulse-wave area (VR) representing an area defined by a waveform of a pulse of the photoelectric pulse wave detected by the photoelectric-pulse-wave detecting device.

BRIEF DESCRIPTION OF THE DRAWINGS

The above and optional objects, features, and advantages of the present invention will be better understood by reading the following detailed description of the preferred embodiment of the invention when considered in conjunction with the accompanying drawings in which.

DETAILED DESCRIPTION OF THE PREFERRED EMBODIMENT

Figure 1:
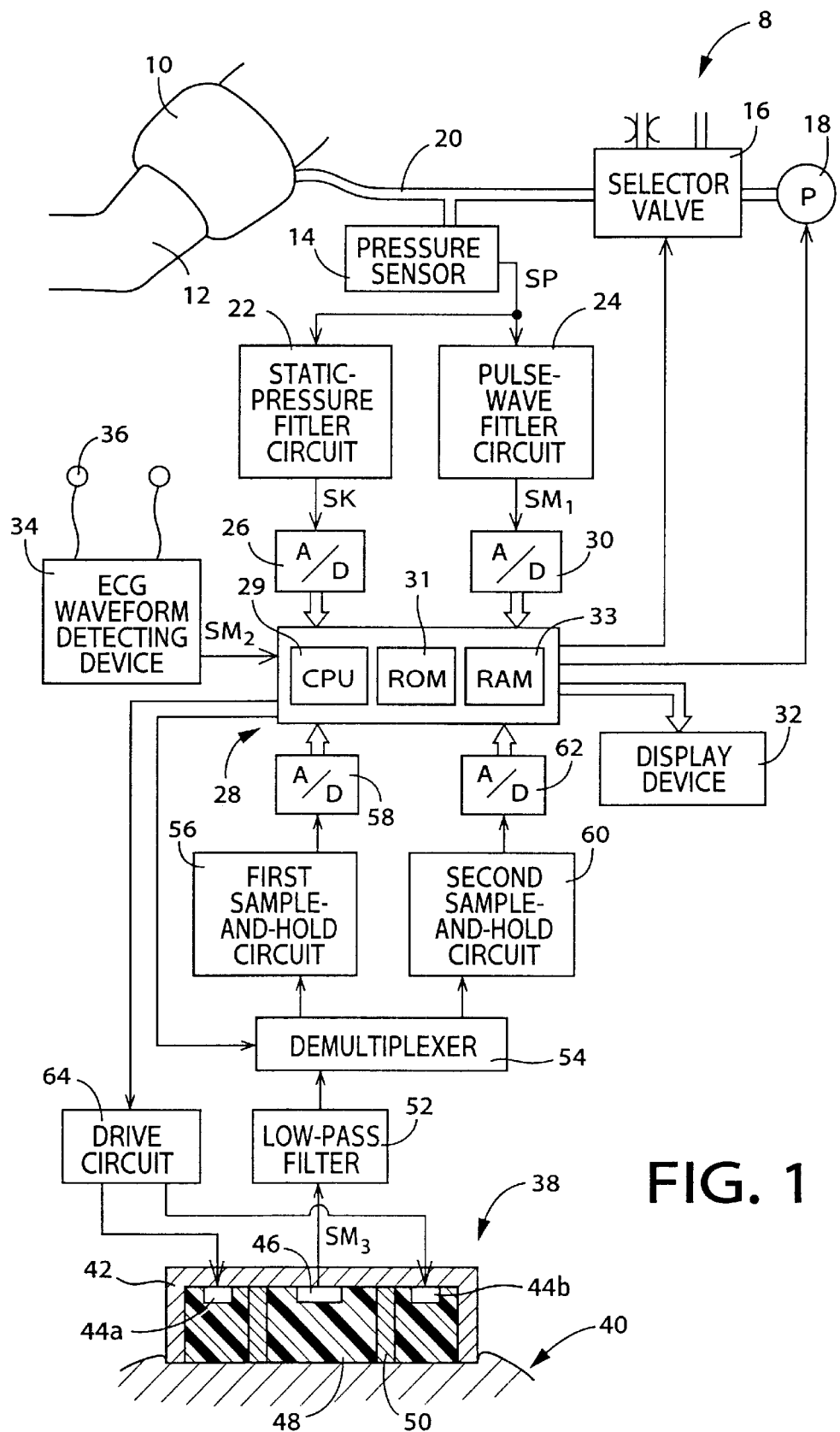
FIG. 1 is a diagrammatic view of a blood pressure monitor apparatus constructed according to one embodiment of the present invention.

Referring first to FIG. 1, there is shown a blood pressure (BP) monitor apparatus 8 constructed according to one embodiment of the present invention. The BP monitor apparatus 8 of FIG. 1 includes an inflatable cuff 10 which has an elongate fabric bag and a rubber bag accommodated in the elongate fabric bag and which is to be wound around an upper arm 12 of a patient, for instance. A pressure sensor 14, a selector valve 16, and an air pump 18 are connected to the cuff 10 via a conduit piping 20.

The selector valve 16 is selectively placed in an inflation position in which the selector valve 16 permits a pressurized air to be supplied from the pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10 and supplies a pressure signal SP representative of the detected pressure to a static-pressure filter circuit 22 and a pulse-wave filter circuit 24. The static-pressure filter circuit 22 includes a low-pass filter and transmits a static component of the signal SP as a cuff-pressure signal SK representative of a static cuff pressure Pc to an electronic control device 28 via a first analog-to-digital (A/D) converter 26.

The pulse-wave filter circuit 24 has a band-pass filter and transmits an oscillating component of the pressure signal SP as a pulse-wave signal $SM_1$, to the electronic control device 28 via a second analog-to-digital (A/D) converter 30. The pulse-wave signal $SM_1$ represents a pulse wave, i.e., an oscillatory pressure wave which is produced from a brachial artery (not shown) of the patient in synchronism with the heartbeat of the patient and is transmitted to the cuff 10.

The electronic control device 28 is constituted by a so-called microcomputer which includes a central processing unit (CPU) 29, a read only memory (ROM) 31, a random access memory (RAM) 33, and an input and output (I/O) port not shown. The CPU 29 performs signal processing operations according to control programs stored in the ROM by utilizing a temporary data storage function of the RAM 33, generates drive signals through the I/O port for controlling the selector valve 16 and the air pump 18, and outputs a display signal to a display device 32 through the I/O port.

The BP monitor apparatus 8 further includes an electronic cardiographic-waveform (ECG-waveform) detecting device 34, and a photoelectric-pulse-wave detecting probe 38 (hereinafter simply referred to as "probe") which is employed as a pulse oximeter. The ECG-waveform detecting device 34 detects an ECG waveform, i.e., electrocardiogram, representative of an action potential of a cardiac muscle of the subject, through a plurality of electrodes 36 attached to predetermined portions of the subject, and supplies an ECG waveform signal $SM_2$ representative of the detected ECG waveform to the electronic control device 28. The ECG-waveform detecting device 34 is used for detecting a Q-wave or an R wave of the ECG waveform corresponding to a time point when the output of the blood from the heart to the aorta of the subject is started. The ECG-waveform detecting device 34 functions as a first pulse wave detecting device.

The probe 38 functions as a second pulse wave detecting device or a peripheral pulse-wave detecting device for detecting a pulse wave which propagates to a peripheral artery including blood capillaries. The probe 38 is worn on a skin or a body surface 40 of the subject such as an end portion of a finger of the subject by means of a band (not shown), such that the probe 38 is held in close contact with the body surface 40. The probe 38 includes a container-like housing 42 which opens in a certain direction, first and second light-emitting elements 44a, 44b provided by light-emitting diodes (LED), for instance, and disposed on an outer peripheral portion of an inner bottom surface of the housing 42 (hereinafter simply referred to as "light-emitting elements 44 in the case where the first and second light-emitting elements 44a, 44b need not be distinguished from each other), a light-receiving element 46 provided by a photodiode or a phototransister and disposed on a central portion of the inner bottom surface of the housing 42, a transparent resin 48 which is integrally disposed in the housing 42 to cover the light-emitting elements 44 and the light-receiving element 46, and an annular shade member 50 which is disposed between the light-emitting elements 44 and the light-receiving element 46 for preventing the lights emitted from the light-emitting elements 44 toward the body surface 40 and reflected by the body surface 40, from being received by the light-receiving element 46.

The first light-emitting elements 44a emit a red light having a wavelength of about 660 nm while the second light-emitting elements 44b emit an infrared light having a wavelength of about 800 nm. The first and second light-emitting elements 44a, 44b alternately emit the red light and the infrared light at a predetermined frequency for a predetermined time period. The lights emitted from the light-emitting elements 44 toward the body surface 40 are reflected from a body portion of the subject where blood capillaries are densely located, and the reflected lights are received by the common light-receiving element 46. The wavelength values of the lights respectively emitted by the first and second light-emitting elements 44a, 44b are not limited to those described above. The first light-emitting elements 44a emit a light having a wavelength at which the absorption coefficients of the light with respect to the oxygenerated hemoglobin and the reduced hemoglobin are considerably different from each other, while the second light-emitting elements 44b emit a light having a wavelength at which the absorption coefficients of the light with respect to the oxygenated hemoglobin and the reduced hemoglobin are substantially the same with each other. In other words, the second light-emitting elements 44b emit a light having a wavelength at which the light is reflected by both of the oxygenerated hemoglobin and the reduced hemoglobin.

The light-receiving element 46 outputs, through a low-pass filter 52, a photoelectric pulse-wave signal $SM_3$ representative of an amount of the received light. The light-receiving element 46 is connected to the low-pass filter 52 via an amplifier, for instance. The low-pass filer 52 eliminates, from the photoelectric pulse-wave signal $SM_3$ input thereto, a noise having a frequency higher than that of the pulse wave, and outputs the noise-free signal $SM_3$ to a demultiplexer 54. The photoelectric pulse wave represented by the photoelectric pulse-wave signal $SM_3$ is a volume pulse wave produced in synchronism with a pulse of the patient, and corresponds to a pulse-synchronous wave.

The demultiplexer 54 is alternately switched according to signals supplied thereto from the electronic control device 28 in synchronism with the light emissions of the first and second light-emitting elements 44a, 44b. The demultiplexer 54 successively supplies, to the I/O port (not shown) of the electronic control device 28, an electric signal SMR representative of the red light through a first sample-and-hold circuit 56 and an A/D converter 58, and an electric signal $SM_{IR}$ representative of the infrared light through a second sample-and-hold circuit 60 and an A/D converter 62. The first and second sample-and-hold circuits 56, 60 respectively hold the current electric signals SMR, $SM_{IR}$ input thereto until the previous electric signals SMR, $SM_{IR}$ have been converted by the respective A/D converters 58, 62.

In the electronic control device 28, the CPU 29 effects a measuring operation according to control programs stored in the ROM 31 by utilizing a temporary-storage function of the RAM 33. More specifically described, the CPU 29 outputs a control signal SLV to a drive circuit 64 for causing the light-emitting elements 44a, 44b to alternately emit the red and infrared lights at a predetermined frequency for a predetermined time period. The CPU 29 also outputs a switch signal SC in synchronism with the light emissions of the light-emitting elements 44a, 44b, so that the demultiplexer 54 is alternately switched to supply the electric signal $SM_R$ to the first sample-and-hold circuit 56 and the electric signal $SM_{IR}$ to the second sample-and-hold circuit 60. The CPU 29 determines an oxygen saturation in the blood of the subject based on respective amplitudes of the signals $SM_R$, $SM_{IR}$ according to a predetermined mathematical expression. The blood oxygen saturation is determined according to a method disclosed in U.S. Pat. No. 5,131,400 assigned to the assignee of the present invention.

Figure 2:
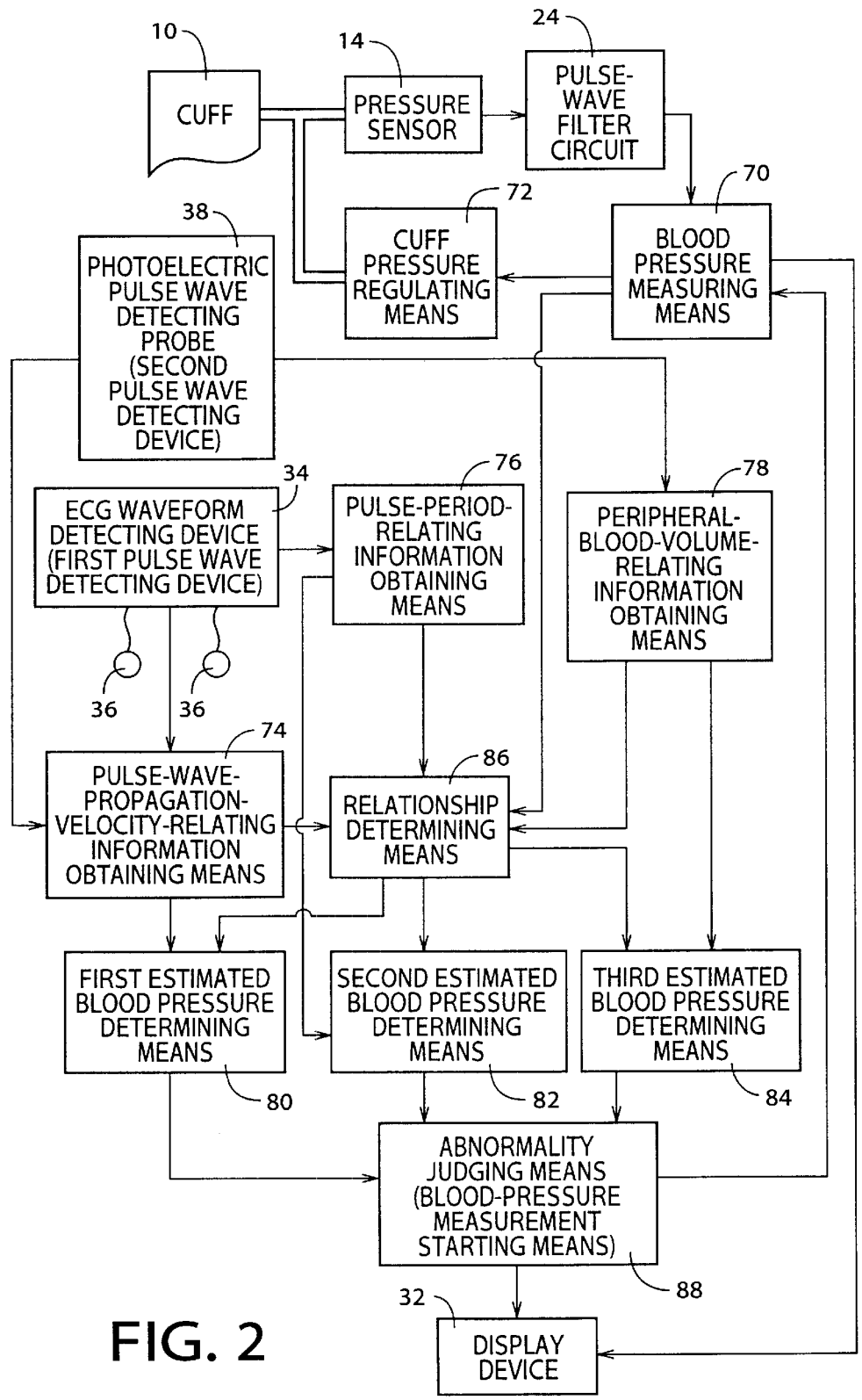
FIG. 2 is a block diagram for illustrating essential functions of an electronic control device of the apparatus of FIG. 1.

As illustrated in FIG. 2 showing essential functions of the electronic control device 28 of the BP monitor apparatus 8 of the present embodiment, the BP monitor apparatus 8 includes blood-pressure (BP) measuring means 70, cuff-pressure regulating means 72, pulse-wave-propagation-velocity-relating information obtaining means 74, pulse-period-relating information obtaining means 76, peripheral-blood-volume-relating information obtaining means 78, first estimated blood pressure determining means 80, second estimated blood pressure determining means 82, third estimated blood pressure determining means 84, relationship determining means 86, and abnormality judging means 88.

The BP measuring means 70 measures a systolic blood pressure $BP_{SYS}$, a mean blood pressure $BP_{MEAN}$, and a diastolic blood pressure $BP_{DIA}$ of the subject according to a known oscillometric method. Described in detail, after the pressure in the cuff 10 wound around on the upper arm of the subject is quickly increased up to a predetermined target value $P_{CM}$ (e.g., about 180 mmHg) by the cuff pressure regulating means 72, the pressure in the cuff 10 is slowly lowered at a rate of about 3 mmHg/sec. The blood pressure values $BP_{SYS}$, $BP_{MEAN, BPDIA}$ are determined on the basis of the change of respective amplitudes of successive pulses of the pulse-wave signal $SM_1$ obtained while the cuff pressure is slowly lowered. The determined blood pressure values $BP_{SYS}$, $BP_{MEAN, BPDIA}$ are indicated on the display 32.

Figure 3:
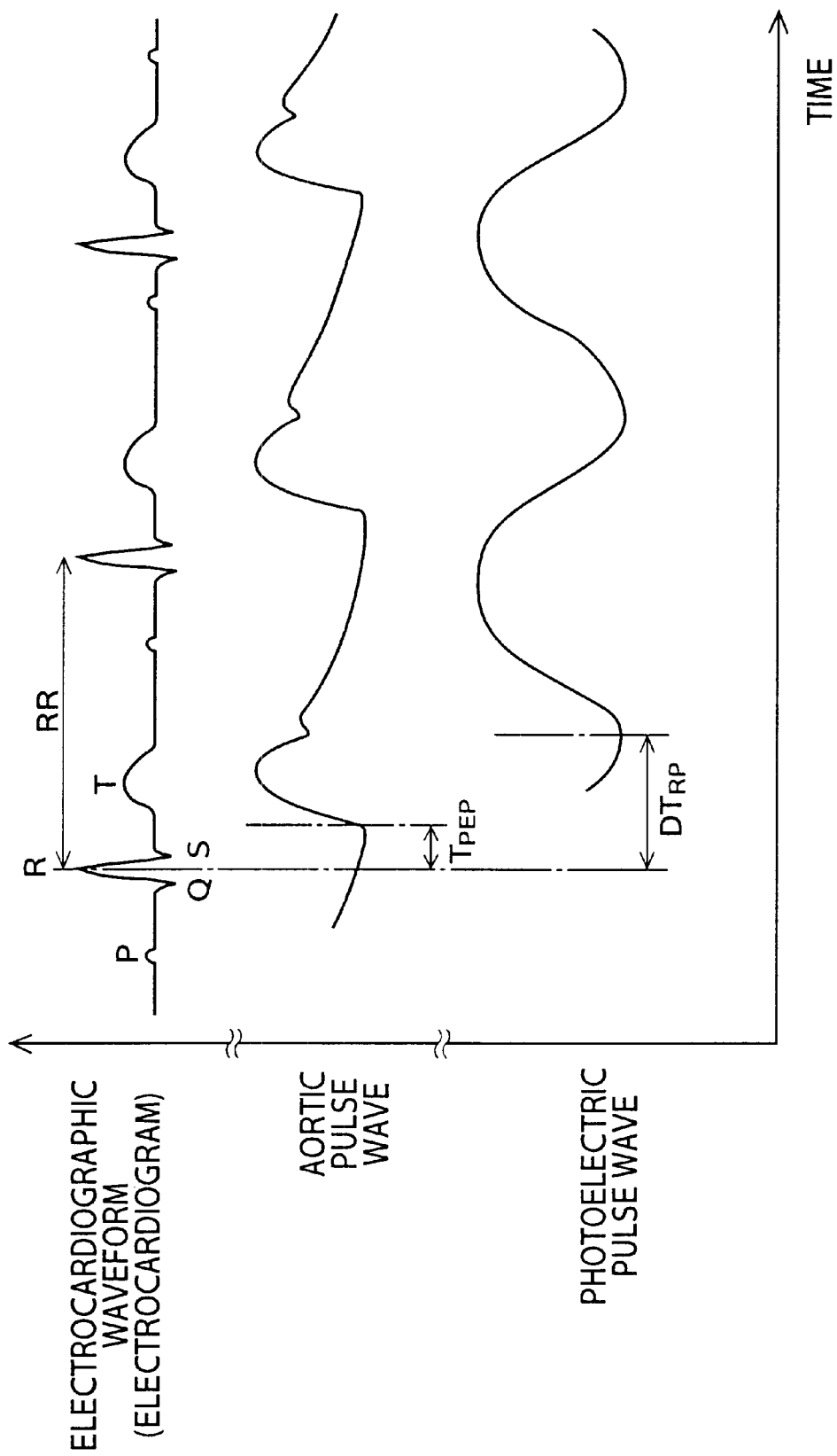
FIG. 3 is a view showing a pulse-wave propagation time $DT_{RP}$ obtained by the operation of the electronic control device of the blood pressure monitor apparatus of FIG. 1.

The pulse-wave-propagation-velocity-relating information obtaining means 74 includes time-difference calculating means for successively calculating, as a pulse-wave propagation time $DT_{RP}$, a time difference between a predetermined point (e.g., R-wave) of the ECG waveform of each of periodic pulses successively detected by the ECG-waveform detecting device 34 and a predetermined point (e.g., rising point or lowest point) of the waveform of a corresponding one of periodic pulses of the photoelectric pulse wave detected by the probe 38, as shown in FIG. 3. The pulse-wave-propagation-velocity-relating information obtaining means 74 successively determines a pulse-wave propagation velocity $V_m$ (m/sec) of the pulse wave which propagates in the artery of the subject based on the calculated pulse-wave propagation time $DT_{RP}$, according to the following expression (1) pre-stored in the ROM 31:

$$V_m = L/(DT_{RP} - T_{PEP}) \quad (1)$$

where L(m) is a length of the artery as measured from the left ventricle to the position at which the probe 38 is attached via the aorta, $T_{PEP}$ (sec) is a pre-ejection period between the R-wave of ECG waveform of each pulse and the lowest point of the waveform of a corresponding pulse of the photoelectric pulse wave. The values L and $T_{PEP}$ are constants, respectively, and are empirically obtained in advance.

Figure 4:
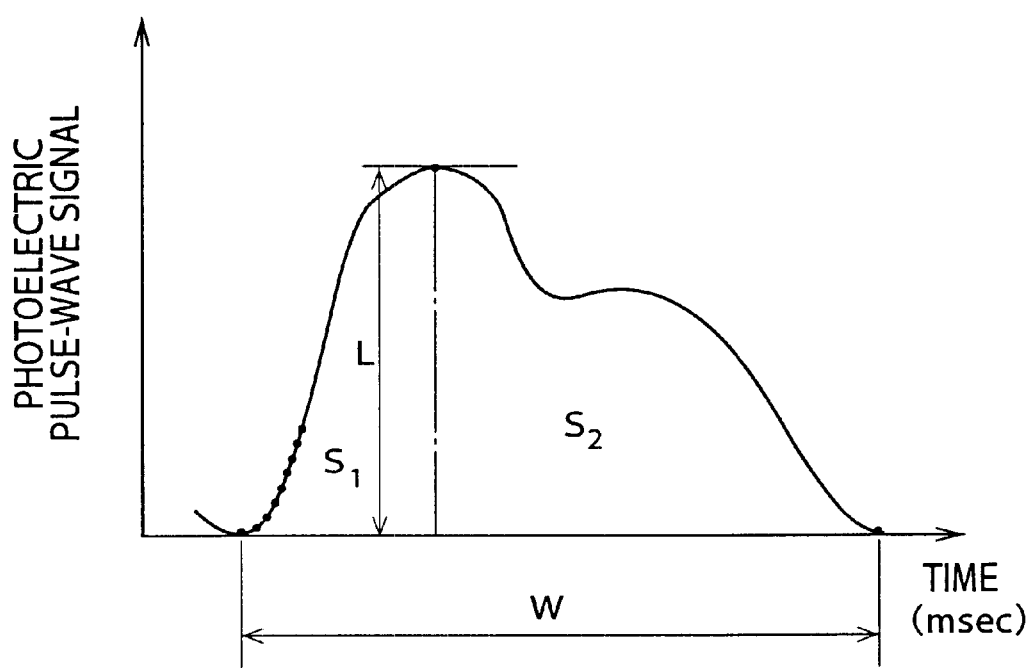
FIG. 4 is a view for explaining normalization to obtain a normalized pulse-wave area VR.

The pulse-period-relating information obtaining means 76 successively obtains information relating to a pulse period of the subject, such as a pulse period RR, by measuring an interval between predetermined points (e.g., R-waves) of successive two pulses of the ECG waveform detected by the ECG-waveform detecting device 34. The peripheral-blood-volume-relating information obtaining means 78 successively obtains information relating to a volume of the blood flowing in the peripheral body portion of the subject. For instance, the peripheral-blood-volume-relating information obtaining means 78 determines an area VR which is defined by a waveform of each of successive pulses of the photoelectric pulse-wave signal $SM_2$ and is normalized based on a period W and an amplitude L of the each pulse of the photoelectric pulse-wave signal $SM_2$. As shown in the graph of FIG. 4, the waveform of each pulse of the photoelectric pulse-wave signal $SM_2$ is defined by a series of data points indicative of respective instantaneous magnitudes of the photoelectric pulse-wave signal $SM_2$ which are input to the control device 28 at a predetermined interval such as several milliseconds to several tens of milliseconds. A pulse-wave area S ($=S_1+S_2$) is obtained by integrating, in the period W of the pulse of the photoelectric pulse-wave signal $SM_2$, the respective magnitudes of the pulse of the signal $SM_2$, and then the normalized pulse-wave area VR is calculated according to the following expression: VR=S/(W×L). The normalized pulse-wave area VR is a dimensionless value indicative of a ratio of the pulse-wave area S to an area defined by the period W and the amplitude of L of the each pulse of the photoelectric pulse wave. The normalized pulse-wave area represents a volume of blood flowing in the peripheral body portion of the subject. A symbol % MAP may be used in place of the symbol VR.

The first estimated blood pressure determining means 80 successively determines a first estimated blood pressure EBP1 based on the pulse-wave-propagation-velocity-relating information such as the pulse-wave propagation-time value $DT_{RP}$ successively obtained by the pulse-wave propagation-velocity-relating information obtaining means 74, according to a predetermined relationship between first estimated blood pressure EBP1 and pulse-wave-propagation-velocity-relating information $DT_{RP}$, which relationship is represented by the following expression (2):

$$EBP1 = \alpha_1 (1/DT_{RP}) + \beta_1 \quad (2)$$

Since the pulse-wave propagation time $DT_{RP}$ decreases with an increase of the blood pressure, in other words, the value $(1/DT_{RP})$ in the above expression (2) increases with an increase of the blood pressure, the coefficient $\alpha_1$ in the expression (2) is a positive value.

The second estimated blood pressure determining means 82 successively determines a second estimated blood pressure EBP2 based on the pulse-period-relating information such as the pulse period value RR successively obtained by the pulse-period-relating information obtaining means 76, according to a predetermined relationship between second estimated blood pressure EBP2 and pulse-period-relating information RR, which relationship is determined according to the following expression (3):

$$EBP2 = \alpha_2 RR + \beta_2 \quad (3)$$

Since the pulse period RR decreases with an increase of the blood pressure, the coefficient $\alpha_2$ in the above expression (3) is a negative value.

The third estimated blood pressure determining means 84 successively determines a third estimated blood pressure EBP3 based on the peripheral blood-volume-relating information such as the normalized pulse-wave area value VR successively obtained by the peripheral-blood-volume-relating information obtaining means 78, according to a predetermined relationship between third estimated blood pressure EBP3 and peripheral-blood-volume-relating information VR, which relationship is represented by the following expression (4):

$$EBP3 = \alpha_3 VR + \beta_3 \qquad (4)$$

Since the normalized pulse-wave area VR increases with an increase of the blood pressure, the coefficient $\alpha_3$ in the above expression (4) is a positive value.

The relationship determining means 86 determines the coefficients $\alpha_1$, $\beta_1$ in the expression (2), the coefficients $\alpha_2$, $\beta_2$ in the expression (3), and the coefficients $\alpha_3$, $\beta_3$ in the expression (4), respectively, based on the systolic blood pressure value $BP_{SYS}$ measured by the blood pressure measuring means 70 and the corresponding one of the pulse-wave-propagation-velocity-relating information, the pulse-period-relating information, and the peripheral-blood-volume-relating information obtained during each blood pressure measurement. For instance, the relationship determining means 86 determines the coefficients $\alpha_1$, $\beta_1$, in the above expression (2) based on the pulse-wave propagation time $DT_{RP}$ obtained by the pulse-wave-propagation-velocity-relating information obtaining means 74 in the current blood pressure measurement. Described in detail, either one of the coefficients $\alpha_1$ and $\beta_1$ in the above expression (2) is determined or changed in advance based on the systolic blood pressure value $BP_{SYS}$ measured by the blood pressure measuring means 70 and the pulse-wave propagation time $DT_{RP}$ obtained during the current blood pressure measurement. Alternatively, the coefficients $\alpha_1$, $\beta_1$ in the expression (2) may be predetermined such that the coefficients $\alpha_1$, $\beta_1$ satisfy a relationship between one set of data consisting of the systolic blood pressure value $BP_{SYS}$ currently measured by the blood pressure measuring means 70 and the pulse-wave propagation time $DT_{RP}$ obtained in the current blood pressure measurement and another set of data consisting of the systolic blood pressure value $BP_{SYS}$ and the pulse-wave propagation time $DT_{RP}$ which have been obtained in the prior blood pressure measurement. In place of the systolic blood pressure $BP_{SYS}$, the mean blood pressure $BP_{MEAN}$ or the diastolic blood pressure $BP_{DIA}$ may be employed in determining the coefficients. In other words, when the mean blood pressure $BP_{MEAN}$ is used to determine the coefficients in the above expressions (2)–(4), the value EBP indicates mean blood pressure, while the value EBP indicates the diastolic blood pressure when the diastolic blood pressure $BP_{DIA}$ is used to determine the coefficients.

The abnormality judging means 88 functioning as blood pressure measurement starting means judges that the blood pressure of the subject is abnormal when at least one of the pulse-wave-propagation-velocity-relating information obtained by the pulse-wave-propagation-velocity-relating information obtaining means 74, the pulse-period-relating information obtained by the pulse-period-relating information obtaining means 76, and the peripheral-blood-volume-relating information obtained by the peripheral-blood-volume-relating information obtaining means 78 does not fall within a predetermined common reference range. When the blood pressure of the subject is judged to be abnormal, the abnormality judging means 88 starts a blood pressure measurement of the blood pressure measuring means 70 and indicates, on the display 32, the abnormality of the blood pressure of the subject. Namely, the abnormality judging means 88 starts a blood pressure measurement of the blood pressure measuring means 70 when at least one of the first estimated blood pressure value $EBP_1$ which corresponds, one to one, to the pulse-wave-propagation-velocity-relating information, the second estimated blood pressure value $EBP_2$ which corresponds, one to one, to the pulse-period-relating information, and the third estimated blood pressure value $EBP_3$ which corresponds, one to one, to the peripheral-blood-volume-relating information, is smaller than a predetermined lower limit value $EBP_L$ or greater than a predetermined upper limit value $EBP_U$ of the common reference range.

There will be described the operation of the electronic control device 28 referring to the flow chart of FIG. 5. A control routine of FIG. 5 is effected for determining the relationship between the blood pressure and the pulse-wave propagation time for determining the first estimated blood pressure $EBP_1$, represented by the above expression (2), the relationship between the blood pressure and the pulse period for determining the second estimated blood pressure $EBP_2$, represented by the above expression (3), and the relationship between the blood pressure and the normalized pulse-wave area for determining the third estimated blood pressure $EBP_3$, represented by the above expression (4).

Figure 5:
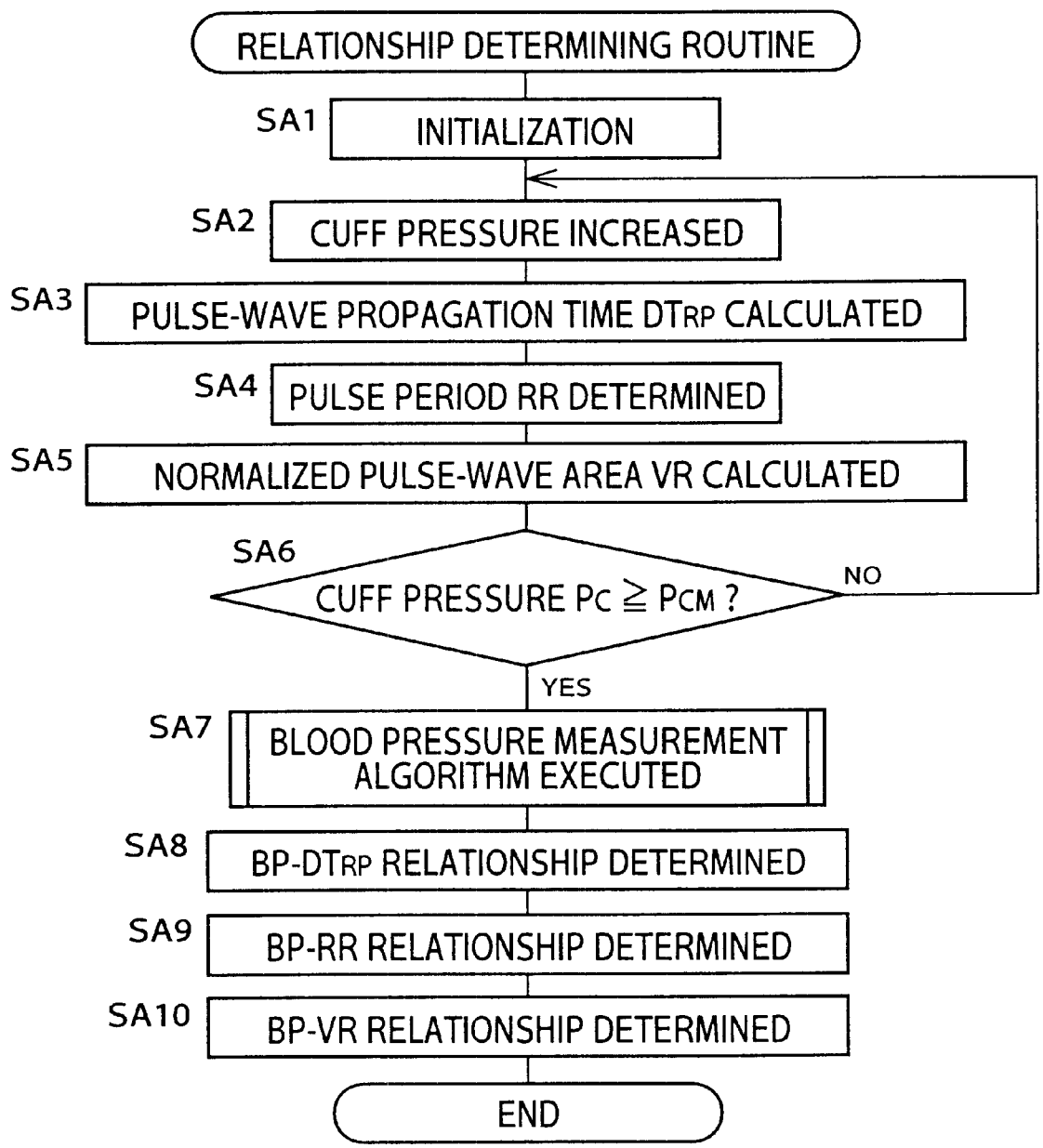
FIG. 5 is a flow chart representing a control routine for determining a relationship between the blood pressure and the pulse-wave propagation time $DT_{RP}$, pulse period RR, or normalized pulse-wave area VR, which control routine is executed by the electronic control device of the apparatus of FIG. 1.

The control routine of FIG. 5 is initiated with Step SA1 in which counters and registers (not shown) are reset. Step SA1 is followed by Step SA2 corresponding to the cuff pressure regulating means 72 to quickly increase the cuff pressure for effecting a blood pressure measurement, by placing the selector valve 16 to its inflation position and actuating the air pump 18.

Step SA2 is followed by Step SA3 corresponding to the pulse-wave-propagation-velocity-relating information obtaining means 74 to obtain, as the pulse-wave propagation time $DT_{RP}$, a time difference between an R-wave of the ECG waveform of a pulse and a rising point of the waveform of a corresponding pulse of the photoelectric pulse wave detected by the probe 38. Step SA3 is followed by Step SA4 corresponding to the pulse-period-relating information obtaining means 76 to obtain the pulse period RR by measuring an interval between the R-waves of successive two pulses of the ECG waveform. Step SA4 is followed by Step SA5 corresponding to the peripheral-blood-volume-relating information obtaining means 78 to obtain a pulse-wave area S, a period W, an amplitude L of a pulse of the photoelectric pulse wave obtained based on the photoelectric pulse-wave signal $SM_2$ (shown in the graph of FIG. 4) detected by the probe 38. On the basis of the obtained pulse-wave area S, period W, and amplitude L of one pulse of the photoelectric pulse wave, a normalized pulse-wave area VR is calculated according to the expression VR=S/(W×L).

The control flow then goes to Step SA6 to judge whether or not the cuff pressure Pc is increased up to or higher than a predetermined target value PCM (e.g., 180 mmHg) If a negative decision is made in Step SA6, the control flow goes back to Step SA2 so as to continue the increasing of the cuff pressure $P_c$. If the cuff pressure $P_c$ is equal to or higher than the target value $P_{CM}$, an affirmative decision is made in Step SA6 and the control flow goes to Step SA7 corresponding to the blood pressure measuring means 70 to perform a blood pressure measuring algorithm. Described in detail, the air pump 18 is turned off and the selector valve 16 is switched from the inflation position to its slow-deflation position where the selector valve 16 permits the pressurized air to be slowly discharged from the cuff 10, so that the pressure in the cuff 10 is slowly decreased at a predetermined rate of 3 mmHg/sec. A systolic blood pressure $BP_{SYS}$, a mean blood pressure $BP_{MEAN}$, and a-diastolic blood pressure are determined based on the variation of amplitudes of successive pulses of the pulse wave represented by the pulse-wave signal $SM_1$, obtained during the slow decreasing of the cuff pressure, according to a well-known oscillometric blood pressure determining algorithm. The thus determined blood pressure values $BP_{SYS}$, $BP_{MEAN, BPDIA}$ are indicated on the display device 32, and the selector valve 16 is switched from the slow-deflation position to its rapid-deflation position, whereby the pressure in the cuff 10 is rapidly lowered.

Step SA7 is followed by Steps SA8 through Step SA10 corresponding to the relationship determining means 86. In Step SA8, the control device 28 determines a relationship between the pulse-wave propagation time and the blood pressure. Namely, the coefficients $\alpha_1$, $\beta_1$ in the above expression (2) are determined based on one set of data consisting of the pulse-wave propagation time value $DT_{RP}$ calculated in Step SA3 and the systolic blood pressure value $BP_{SYS}$ determined in Step SA7 which are obtained in the current control cycle, and another set of data consisting of the pulse-wave propagation time value $DT_{RP}$ and the systolic blood pressure value $BP_{DIA}$ respectively obtained in Step SA7 and Step SA3 of the prior control cycle. Step SA8 is followed by Step SA9 to determine a relationship between the pulse period and the blood pressure, i.e., the coefficients $\alpha_2$, $\beta_2$ in the above expression (3) based on one set of data consisting of the pulse period value RR and the systolic blood pressure value $BP_{SYS}$ respectively obtained in Step SA4 and Step SA7 of the current control cycle, and another set of data consisting of the pulse period value RR and the systolic blood pressure value $BP_{SYS}$ respectively obtained in Step SA4 and Step SA7 of the prior control cycle. SA9 is followed by Step SA10 to determine a relationship between the normalized pulse-wave area and the blood pressure, i.e., the coefficients $\alpha_3$, $\beta_3$ in the above expression (4) based on one set of data consisting of the normalized pulse-wave area value VR and the systolic blood pressure value $BP_{SYS}$ respectively obtained in Step SA5 and Step SA7 of the current control cycle, and another set of data consisting of the normalized pulse-wave area value VR and the systolic blood pressure value $BP_{SYS}$ respectively obtained in Step SA5 and Step SA7 of the prior control cycle.

Figure 6:
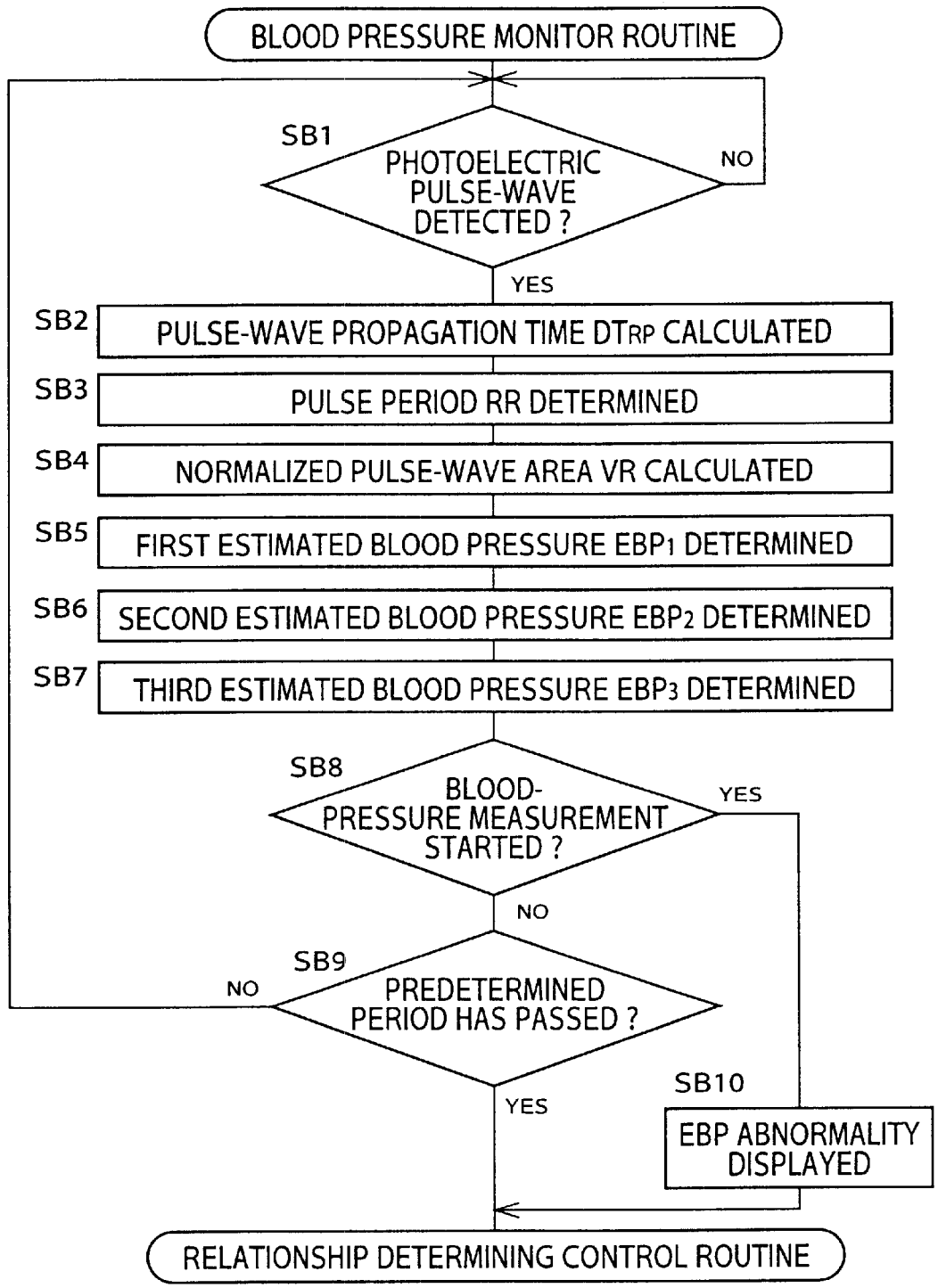
FIG. 6 is a flow chart representing a control routine for monitoring a blood pressure of the subject executed by the electronic control device of the apparatus of FIG. 1.

After the coefficients in the above expressions (2)–(4) are determined as described above, the electronic control device 28 executes a blood pressure monitor routine as indicated by a flow chat of FIG. 6. The control routine of FIG. 6 is initiated with Step SB1 to judge whether or not the R-wave of the ECG waveform and the photoelectric pulse wave have been detected. As long as a negative judgment is made in Step SB1, this step is repeatedly implemented. If an affirmative judgment is made in Step SB1, the control flow goes to Step SB2 corresponding to the pulse-wave-propagation-velocity-relating information obtaining means 74 to obtain a pulse-wave propagation time $DT_{RP}$ with respect to the R-wave of the ECG waveform and the photoelectric pulse wave which have been read in Step SB1, in the same manner as carried out in Step SA3 of the control routine of FIG. 5.

Step SB2 is followed by Step SB3 corresponding to the pulse-period-relating information obtaining means 76 to obtain a pulse period RR based on the interval between the R-waves of successive two pulses of the ECG waveform detected in Step SB1. SB3 is followed by Step SB4 corresponding to the peripheral-blood-volume-relating information obtaining means 78 to obtain a normalized pulse-wave area VR based on the photoelectric pulse wave read in Step SB1, in the same manner as carried out in Step SA5 of FIG. 5.

The control flow then goes to Step SB5 corresponding to the first estimated blood pressure determining means 80 to determine a first estimated blood pressure $EBP_1$ based on the pulse-wave propagation time $DT_{RP}$ calculated in Step SB2, according to the relationship which is represented by the above expression (2) and determined in Step SA8 of the control routine of FIG. 5. Step SB5 is followed by Step SB6 corresponding to the second estimated blood pressure determining means 82 to determine a second estimated blood pressure $EBP_2$ based on the pulse period RR obtained in Step SB3, according to the relationship which is represented by the above expression (3) and determined in Step SA9 of the control routine of FIG. 5. Step SB6 is followed by Step SB7 corresponding to the third estimated blood pressure determining means 84 to determine a third estimated blood pressure $EBP_3$ based on the normalized pulse-wave area VR obtained in Step SB4, according to the relationship which is represented by the above expression (4) and determined in Sep SA10 of the control routine of FIG. 5.

The control flow then goes to Step SB8 corresponding to the abnormality judging means 88 to judge whether or not at least one of the estimated blood pressure values $EBP_1$, $EBP_2$, $EBP_3$ is greater than an upper limit value $EBP_H$ or smaller than a lower limit value $EBP_L$ of a predetermined reference range. If a negative judgment is made in Step SB8, step SB9 is implemented to judge whether or not a predetermined period (e.g., 15 to 20 minutes), that is, a calibration period, has passed after the control routine of FIG. 5 for determining the relationships represented by the expressions (2)–(4) was implemented. If a negative judgment is made in Step SB9, the control flow goes back to Step SB1 and the following steps so as to repeat the blood pressure monitor routine.

On the other hand, if an affirmative judgment is made in Step SB9, the relationship determining routine of FIG. 5 is implemented to update the coefficients in the above expressions (2)–(4). If an affirmative judgment is made in Step SB8, the control flow goes to Step SB10 to indicate abnormality of the blood pressure on the display 32, and implement the relationship determining routine of FIG. 5 for effecting a reliable blood pressure measurement using the cuff 10 and updating the coefficients in the expressions (2)–(4).

In the present embodiment, the abnormality judging means 88 judges that the blood pressure of the subject is abnormal when at least one of the first estimated blood pressure value EBP1 determined by the first estimated blood pressure determining means 80 (Step SB5), the second estimated blood pressure value EBP2 determined by the second estimated blood pressure determining means (Step SB6), and the third estimated blood pressure value EBP3 determined by the third blood pressure determining means (Step SB7) is smaller than the lower limit value $EBP_L$ or greater than the upper limit value $EBP_H$ of the common reference range. According to this arrangement, even if the first estimated blood pressure value EBP1 determined based on the pulse-wave propagation time $DT_{RP}$ may fall within the reference range having the lower limit value $EBP_L$ and the upper limit value $EBP_H$, the abnormality judging means 88 judges that the blood pressure of the subject is abnormal when the second estimated blood pressure value EBP2 determined based on the pulse period RR or the third estimated blood pressure value EBP3 determined based on the normalized pulse-wave area VR does not fall within the reference range. Accordingly, the present arrangement is capable of accurately detecting the change of the blood pressure over the entire blood pressure range.

In the present embodiment, when the abnormality judging means 88 (Step SB8) judges that the blood pressure of the subject is abnormal, the abnormality judging means 88 starts the blood pressure measurement of the blood pressure measuring means 70 (Step SA7). In the present arrangement, even if the first estimated blood pressure value EBP1 determined based on the pulse-wave propagation time $DT_{RP}$ may fall within the reference range having the lower limit value $EBP_L$ and the upper limit value $EBP_H$, the blood pressure measurement of the measuring means 70 (Step SA7) is executed when the second estimated blood pressure value EBP2 determined based on the pulse period RR or the third estimated blood pressure value EBP3 determined based on the normalized pulse-wave area VR does not fall within the reference range. Accordingly, the present arrangement is capable of quickly and accurately obtaining reliable blood pressure values when the blood pressure of the subject has changed.

While the present invention has been described in its presently preferred embodiment, it is to be understood that the invention may be otherwise modified.

Each of the coefficients $\alpha_1$, $\alpha_2$, $\alpha_3$ in the above expressions (2)–(4) may be changed based on a predetermined relationship between a difference of a blood pressure BP measured by the blood pressure measuring means 70 and an estimated blood pressure EBP determined immediately after the blood pressure BP has measured, and an amount of change of each coefficient $\alpha_1$, $\alpha_2$, $\alpha_3$. The following Table 1 shows one example of the relationship, i.e., a relationship used in changing the coefficient $\alpha_1$, in the above expression (2).

TABLE 1

| BP - EBP1 (mmHg) | $\alpha_1$ |
| --- | --- |
| not less than +30 | $\alpha_1 - 0.2$ |
| not less than +15 and less than +30 | $\alpha_1 - 0.1$ |
| not less than −15 and less than +15 | (not changed) |
| not less than −30 and less than −15 | $\alpha_1 + 0.1$ |
| less than −30 | $\alpha_1 + 0.2$ |

The coefficients in the above formulas (2)–(4) may be determined by utilizing a pre-established neural network, or a fuzzy theory. For instance, the coefficient $\alpha_1$ in the above expression (2) is determined by utilizing a pre-established neural network into which other sorts of blood pressure-relating information, such as pulse-period-relating information, peripheral-blood-pressure-volume-relating information, arterial sclerosis degree, and pulse pressure, are input.

In the illustrated embodiment, the peripheral-blood-volume-relating information 78 obtains, as the peripheral-blood-volume-relating information, the normalized pulse-wave area VR which is obtained by normalizing a pulse-wave area S defined by a waveform of a pulse of the photoelectric pulse wave. The pulse-wave area S of the waveform of one pulse of the photoelectric pulse wave may be used, as the peripheral-blood-volume-relating information, without being normalized. Alternatively, the amplitude of one pulse of the photoelectric pulse wave may be used as the peripheral-blood-volume-relating information.

In the illustrated embodiment, the abnormality judging means 88 judges whether or not at least one of the first estimated blood pressure value EBP1 determined based on the pulse-wave propagation time $DT_{RP}$, the second estimated blood pressure value EBP2 determined based on the pulse period RR, and the third estimated blood pressure value EBP3 determined based on the normalized pulse-wave area VR falls within the common reference range having the lower limit value $EBP_L$ and the upper limit value $EBP_H$. The abnormality judging means 88 may be arranged to judge whether or not at least one of the pulse-wave-propagation-velocity-relating information, the pulse-period-relating information, and the peripheral-blood-volume-relating information falls within a corresponding one of a first, a second, and a third reference range, respectively, which are different from one another.

The BP monitor apparatus of the illustrated embodiment is arranged to control the display device 32 to indicate abnormality of the blood pressure of the subject, and to effect the blood pressure measurement by the blood pressure measuring means 70 when the abnormality judging means 88 judges abnormality of the blood pressure. The BP monitor apparatus may be arranged to effect only one of the indication of abnormality of the blood pressure on the display device 32 and the blood pressure measurement by the blood pressure measuring means 70.

In the illustrated embodiment, the abnormality judging means 88 judges whether or not at least one of the estimated blood pressure EBP1, EBP2, EBP3 falls within the reference range having a predetermined upper limit value and a predetermined lower limit value. However, the abnormality judging means 88 may be modified to determine upper and lower limit values of a reference range based on a blood pressure value BP obtained in the prior blood pressure measurement using the cuff 10, or a moving average of blood pressure values BP obtained during a predetermined time period.

While the reference range in the illustrated embodiment has the lower limit value $EBP_L$ and the upper limit value $EBP_H$, the reference range may have only one of the lower and upper limit values $EBP_L$, $EBP_H$.

It is to be understood that the present invention may be embodied with other changes, modifications, and improvements that may occur to those skilled in the art without departing from the scope of the invention defined in the attached claims.

What is claimed is:

1. A blood pressure monitor apparatus for monitoring a blood pressure of a living subject, comprising:

pulse-wave-propagation-velocity-relating information obtaining means for successively obtaining pulse-wave-propagation-velocity-relating information which relates to a pulse-wave propagation velocity at which a pulse wave propagates in an artery of the subject;

pulse-period-relating information obtaining means for successively obtaining pulse-period-relating information which relates to a pulse period of the subject;

peripheral-blood-volume-relating information obtaining means for successively obtaining peripheral-blood-volume-relating information which relates to a volume of blood which flows in a peripheral body portion of the subject; and abnormality judging means for judging that said blood pressure of the subject is abnormal when at least one of said pulse-wave-propagation-velocity-relating information, said pulse-period-relating information, and said peripheral-blood-volume-relating information does not fall within a corresponding one of a first, second and a third reference range, wherein:

said pulse-wave-propagation-velocity-relating information obtaining means comprises first estimated blood pressure determining means for successively determining, as said pulse-wave-propagationvelocity-relating information, a first estimated blood pressure value $EBP_1$, based on a pulse-wave propagation time, by utilizing a predetermined relationship between first estimated blood pressure value $EBP_1$, and pulse-wave propagation time $DT_{RP}$, said relationship being represented by an equation: $EBP_1 = \alpha_1(1/DT_{RP}) + \beta_1$, wherein $\alpha_1$, and $\beta_1$ represent coefficients, said pulse-period-relating information obtaining means comprises second estimated blood pressure determining means for successively determining, as said pulse-period-relating information, a second estimated blood pressure value $EBP_2$, based on a pulse period of the subject, by utilizing a predetermined relationship between second estimated blood pressure value $EBP_2$ and pulse period RR, said relationship being represented by an equation: $EBP_2 = \alpha_2 RR + \beta_2$, wherein $\alpha_2$ and $\beta_2$ represent coefficients, and said peripheral-blood-volume-relating information obtaining means comprises third estimated blood pressure determining means for successively determining, as said peripheral-blood-volume-relating information, a third estimated blood pressure value $EBP_3$, based on a pulse-wave area, by utilizing a predetermined relationship between third estimated blood pressure value $EBP_3$ and pulse-wave area VR, said relationship being represented by an equation: $EBP_3 = \alpha_3 VR + \beta_3$, wherein $\alpha_3$ and $\beta_3$ represent coefficients.

2. A blood pressure monitor apparatus according to claim 1, wherein said pulse-wave-propagation-velocity-relating information obtaining means comprises an electrocardiographic-waveform detecting device which includes a plurality of electrodes adapted to be attached to a body portion of the subject and detects an electrocardiographic waveform indicative of an action potential of a cardiac muscle of the subject through said electrodes, and a photoelectric-pulse-wave detecting device which includes a plurality of light-emitting elements and a light-receiving element, each of said light-emitting elements emitting, toward a body surface of the subject, a light having a wavelength which is reflected by hemoglobin present in the blood of the subject, said light-receiving element receiving the light scattered by the hemoglobin from the body surface of the subject, said photoelectric-pulse-wave detecting device detecting a photoelectric pulse wave indicative of the volume of the blood flowing in the body surface, said pulse-wave propagation time ($DT_{RP}$) representing a time difference between a predetermined point of a pulse of said electrocardiographic waveform detected by said electrocardiographic-waveform detecting device, and a predetermined point of a waveform of a corresponding pulse of said photoelectric pulse wave detected by said photoelectric-pulse-wave detecting device.

3. A blood pressure monitor apparatus according to claim 1, wherein said pulse-period-relating information obtaining means comprises an electrocardiographic-waveform detecting device which includes a plurality of electrodes adapted to be attached to a body portion of the subject and detects an electrocardiographic waveform indicative of an action potential of a cardiac muscle of the subject through said electrodes, said pulse period (RR) representing an interval between successive two R-waves of said electrocardiographic waveform detected by said electrocardiographic-waveform detecting device.

4. A blood pressure monitor apparatus according to claim 1, wherein said peripheral-blood-volume-relating information obtaining means comprises a photoelectric-pulse-wave detecting device which includes a plurality of light-emitting elements and a light-receiving element, each of said light-emitting elements emitting, toward a body surface of the subject, a light having a wavelength which is reflected by hemoglobin present in the blood of the subject, said light-receiving element receiving the light scattered by the hemoglobin from the body surface of the subject, said photoelectric-pulse-wave detecting device detecting a photoelectric pulse wave indicative of the volume of the blood flowing in the body surface, said pulse-wave area (VR) representing an area defined by a waveform of a pulse of said photoelectric pulse wave detected by said photoelectric-pulse-wave detecting device.

* * * * *